(12) United States Patent
Amarilli et al.

(10) Patent No.: US 6,204,423 B1
(45) Date of Patent: Mar. 20, 2001

(54) CATALYTIC COMPOSITION FOR THE PREPARATION OF LONG-CHAIN ALKYLAROMATIC COMPOUNDS

(75) Inventors: Stefano Amarilli, Milan; Carlo Perego, Carnate; Giuseppe Bellussi, Piacenza; Giovanni Colombo, Inveruno, all of (IT)

(73) Assignee: Enichem Augusta Industriale S.r.l., Milan (IT)

( * ) Notice: Subject to any disclaimer, the term of this patent is extended or adjusted under 35 U.S.C. 154(b) by 0 days.

(21) Appl. No.: 08/990,520

(22) Filed: Dec. 15, 1997

Related U.S. Application Data

(63) Continuation of application No. 08/454,562, filed on May 30, 1995, now abandoned.

(30) Foreign Application Priority Data

Jul. 13, 1994 (IT) .................................................. 01451/94

(51) Int. Cl.[7] ........................................................ C07C 2/68
(52) U.S. Cl. ............................................. 585/467; 502/68
(58) Field of Search .............................. 502/63, 64, 68, 502/73, 79; 585/467

(56) References Cited

U.S. PATENT DOCUMENTS

| | | | |
|---|---|---|---|
| 4,176,090 | * | 11/1979 | Vaughan et al. . |
| 4,271,043 | * | 6/1981 | Vaughan et al. . |
| 4,637,991 | * | 1/1987 | Battiste et al. . |
| 4,742,033 | * | 5/1988 | Harris et al. . |
| 4,957,889 | * | 9/1990 | McCauley . |

FOREIGN PATENT DOCUMENTS

| | | | |
|---|---|---|---|
| 0 355 213 | * | 2/1990 | (EP) . |
| 0 400 857 | * | 12/1990 | (EP) . |
| 0 491 520 | * | 6/1992 | (EP) . |
| WO 88/06488 | * | 9/1988 | (WO) . |
| WO 88/06614 | * | 9/1988 | (WO) . |

\* cited by examiner

*Primary Examiner*—Tom Dunn
(74) *Attorney, Agent, or Firm*—Oblon, Spivak, McClelland, Maier & Neustadt, P.C.

(57) ABSTRACT

A description follows of a catalytic composition comprising a mixture of Y zeolite and pillared clay and a process which uses this catalytic composition for the alkylation of aromatic hydrocarbons by means of long-chain linear olefins. The aromatic alkyl compounds thus obtained are useful for the preparation of biodegradable synthetic detergents.

15 Claims, No Drawings

CATALYTIC COMPOSITION FOR THE PREPARATION OF LONG-CHAIN ALKYLAROMATIC COMPOUNDS

This application is a Continuation of application Ser. No. 08/454,562, filed on May 30, 1995, now abandoned.

A catalytic compound is described, comprising a mixture of Y zeolite and a smectite containing alumina pillars together with a process for the alkylation of aromatic hydrocarbons by means of long-chain linear olefins which uses this composition.

Alkylaromatic compounds have numerous industrial applications. Among these the most important relate to their use in the preparation of biodegradable synthetic detergents. Processes for the preparation of aromatic compounds using Friedel-Crafts type catalysts such as for example $AlCl_3$, $BF_3$, $H_2SO_4$ and HF, have been known for some time. These catalysts however obviously have considerable disadvantages not only because they create problems of corrosion of the materials used, but also because of the environmental problems associated with eliminating the waste products.

It was subsequently found that some solid catalysts can be used to carry out the alkylation of aromatic hydrocarbons with olefins giving a production of a similar quality to the above but without the problems of environment and corrosion. Both zeolites and clays suitably treated have therefore been used for this purpose. In the U.S. Pat. No. 2,904,607, for example, for the alkylation of aromatic hydrocarbons with olefins a metallic alumino-silicate is used with pores of 6 . 15 Å. U.S. Pat. No. 3,251,897 describes alkylation with exchanged zeolites in a protonic form or with rare earths. U.S. Pat. No. 3,417,148 relates to the alkylation of an aromatic compound, for example benzene, toluene or xylenes, with an olefin, catalyzed by a crystalline aluminosilicate chemically combined with metallic fluorides.

In particular, the Journal of Catalysis, 5, 81–98, (1966), by P. B. Venuto et al., describes the use of the Y zeolite for the alkylation of aromatic substrates with a wide variety of alkylating agents among which are olefins. In the Journal of Catalysis, 26, 303–312, (1972), by T. Yashima et al., a Y zeolite, exchanged with alkaline cations, is used for the alkylation of toluene with methanol and formaldehyde. Y zeolites are also used in the transalkylation of alkylaromatics, as described for example in the Journal of Catalysis, 140, 384–394, 1993.

Other materials known as alkylation catalysts are natural or synthetic clays exchanged with metallic cations. In U.S. Pat. No. 4,046,826, for example, a natural trioctahedric clay or synthetic clay exchanged with metallic cations is used for the alkylation of benzene with long-chain olefins. Patent U.S. Pat. No. 4,499,319 claims the use of clays stratified with a lamellar structure, such as montmorillonite, exchanged with metallic cations such as chromium and aluminium, for the alkylation of aromatic compounds with alkylating agents containing less than 6 carbon atoms. Synthetic clays exchanged with cations and then suitably activated, useful for the alkylation of aromatic compounds, are described in U.S. Pat. No. 4,075,126.

In EP 353813, natural or synthetic zeolites, amorphous silico-aluminas, clays, or their mixtures, possibly subjected to ion exchange with aluminium salts, chromium or rare earths, are used for the catalytic alkylation of aromatic hydrocarbons with olefins.

Clays exchanged with metallic cations however have proved to have a limited thermal stability. Modified clays called "pillared clays" which, compared to the above materials, are stable even at high temperatures, were subsequently used as alkylation catalysts.

These materials are prepared starting from synthetic or natural clays, such as smectites, vermiculites or bentonites. The clays consist of layers of semi-crystalline aluminosilicates bound to each other by Van der Waals electrostatic forces. The anion charges on the silica layers are neutralized by cations, situated in the interlamellar spaces. These cations, normally $Na^+$ and $Ca^{2+}$, can be exchanged with monomeric, oligomeric or polymeric species deriving from metal hydroxides such as hydroxo-polymer cations $[Al_{13}O_4(OH)_{24}(H_2O)_{12}]^{7+}$ or $[Zr(OH)_2H_2O]_4^{8+}$. These cations act as a separation system of the crystalline silicoaluminate layers, or as a pillaring system. Patent EP 83970 describes the use of a clay in which pillars of alumina are anchored inside the laminar structure for the alkylation of benzene with light olefins. In patent U.S. Pat. No. 5,034,564 a pillared clay containing a metal oxide selected from Al, Zr, La, Ce and Ti as a spacing element of the crystalline layers, coextruded with a binder, is used in alkylation reactions of aromatic hydrocarbons.

In Applied Catal., 14, 69–82 (1985) by M. L. Occelli, a Na-montmorillonite stratified with a system of clusters of aluminium oxide is compared to other types of catalysts in the ethylation reaction of toluene.

U.S. Pat. No. 4742033 describes a cracking catalyst consisting of a pillared clay pretreated with suitable inorganic reagents. This catalyst, possibly mixed with a zeolite, is compared, among others, to a catalyst consisting of 10% by weight of Y zeolite and 90% by weight of a pillared clay, where the clay is bentonite, in the cracking process of hydrocarbons.

It has now been surprisingly found that it is possible to carry out the alkylation of aromatic hydrocarbons with long-chain olefins operating in the presence of a catalytic composition comprising a mixture of a Y zeolite and a suitable pillared clay. This catalytic composition allows better results than those obtained either using each of the elements individually or using a mixture consisting of a Y zeolite and a clay. These better results relate to both the catalyst activity and its duration and also to the selectivity to linear alkylbenzenes.

The present invention therefore relates to a catalytic composition comprising a mixture of Y zeolite and a smectite containing pillars of alumina, with a weight ratio between Y zeolite and smectite with alumina pillars of between 0.1 and 10, excluding the ratio 1:9 when the smectite is bentonite.

In the catalytic mixture the weight ratio between Y zeolite and smectite with alumina pillars is preferably between 0.3 and 1.5.

The Y zeolite which can be used in the present invention is in acid form and is described in U.S. Pat. No. 3,130,007.

Smectites containing pillars of aluminium oxide which can be used in the catalytic composition of the present invention are those which can be obtained by the treatment of a clay of the group of smectites with a solution containing polyoxoaluminium ions, followed by the calcination of the resulting solid, as described for example in the patents U.S. Pat. No. 4,216,188 and U.S. Pat. No. 4,176,090. The smectite is preferably selected from bentonite, montmorillonite and beidellite.

As a typical example, the solution of polyoxoaluminium ions is prepared by adding, at a temperature of between 25 and 100° C., a solution of NaOH to a solution of $AlCl_3$, so that the molar ratio between the reagents is between 1 and 2.5. The resulting mixture is maintained under stirring, at a temperature of between 25 and 100° C., for 1–10 hours. A suspension in water of a clay belonging to the group of smectites, heated to a temperature between 25 and 50° C. is then put in contact with the previously prepared aqueous solution of polyoxoaluminium ions, also known as Kegging ions. The weight ratio between clay and $AlCl_3$ previously used to prepare the solution of polyoxoaluminium ions is between 2 and 5. The mixture thus obtained is maintained under stirring at a temperature of between 25 and 100° C. for 1–60 hours. The pH of the solution is between 3 and 7.

The resulting solid, isolated for example by centrifugation, consists of a clay belonging to the group of smectites inside whose laminar structure the polyoxoaluminium ions have substituted the metallic cations naturally present. This humid material is subjected to calcination at a temperature of between 200 and 700° C., for a period of between 2 and 10 hours, to decompose the polyoxoaluminium ions to give pillars of alumina.

The material resulting from the calcination is therefore a smectite containing alumina pillars, for example a bentonite or a montmorillonite containing pillars of alumina.

The catalytic composition of the present invention is obtained by mixing the Y zeolite and smectite containing pillars of alumina using any of the known mixing techniques. For example the Y zeolite and smectite containing pillars of alumina are mixed in a weight ratio of between 0.1 and 10, excluding the ratio 1:9 when the smectite is bentonite, in the presence of water, and possible a plasticizer. The plasticizer can be for example methylcellulose. In this way a homogeneous paste is produced which is formed, for example, by extrusion, granulation or pelletting, and then calcinated. The calcination can be carried out at a temperature of between 200 and 700° C. for a time of between 2 and 10 hours. During the mixing a binder, for example silica, alumina or silica-alumina may also be added.

According to another form of embodiment the Y zeolite is mixed with the smectite containing polyoxoaluminium ions, in humid form, before being subjected to calcination to decompose the polyoxoaluminium ions to give pillars of alumina. The weight proportion between the components which are mixed depends on the degree of humidity of the smectite containing polyoxoaluminium ions used. The resulting mixture is then subjected to calcination at a temperature of between 200 and 700° C. for 2–10 hours.

These catalytic compositions allow the alkylation of aromatic hydrocarbons by means of long-chain olefins with an improved selectivity to linear alkylation products.

A second object of the present invention therefore relates to a process for the alkylation of aromatic hydrocarbons with linear olefins containing from 8 to 16 carbon atoms, or their mixtures, carried out in a liquid phase, under anhydrous conditions and at a temperature of between 120 and 160° C., in the presence of a catalytic composition comprising a mixture of a Y zeolite and a smectite containing pillars of alumina, with a weight ratio between the Y zeolite and smectite with pillars of alumina of between 0.1 and 10.

Aromatic hydrocarbons which can be alkylated are both monocyclic and polycyclic, also alkylsubstituted. For example benzene, toluene, xylenes, ethylbenzene, naphthalene, methyl-naphthalenes, ethyl-naphthalenes, anthracene can be used. Benzene is the preferred substrate to be alkylated. The olefins are preferably selected from those containing from 10 to 13 carbon atoms, or their mixtures.

The synergetic effect, in terms of activity and duration of the catalyst and in terms of selectivity to linear alkylbenzenes, which is surprisingly obtained by mixing the Y zeolite with the smectite containing pillars of alumina, can be observed when the alkylation process of the present invention is carried out at a temperature of between 120 and 160° C., preferably between 140 and 160° C. The pressure is between 10 and 50 bars, preferably between 20 and 25 bars, and the WHSV is between 0.1 and 10 hours$^{-1}$, preferably between 0.3 and 2 hours$^{-1}$.

Operating under anhydrous conditions is particularly important. The elimination of water from the reagents can be carried out for example by treatment with suitable molecular sieves. The catalyst is preferably preactivated by treatment in a nitrogen flow at a temperature of between 250 and 400° C., preferably between 300 and 350° C., which eliminates the residuous traces of water. The aromatic hydrocarbon and olefin are fed to the reaction reactor in a mixture, in a molar ratio hydrocarbon/olefin between 30 and 1, preferably between 20 and 10.

The olefins can be diluted with n-paraffins containing from 8 to 16 carbon atoms, in a ratio of 1:1 to 1:20.

The process of the present invention can be carried out both in batch and in continuous. With the first method of procedure, the aromatic compound, the olefin and catalytic composition are charged into an autoclave. The pressure is provided by the introduction of an inert gas, for example nitrogen, helium or argon, whereas the olefin is in liquid form. If the olefin is in a gaseous form, a portion of the operating pressure is supplied by the autogenous pressure of the gaseous alkylating agent, whereas the rest is supplied by the presence of the inert gas. When the reaction has finished, the autoclave is cooled to room temperature, the system is depressurized, the autoclave is opened and the reaction mixture is recovered and the desired alkylaromatic is isolated with the conventional techniques, for example fractional distillation.

When the alkylation of the present invention is carried out in a continuous form, the catalytic composition is charged into a reactor, for example tubular, brought to operating pressure and heated to the desired temperature. The reagents are continuously passed through the catalytic bed at the selected space velocity. The catalytic composition can be kept in the reactor in the form of a fixed bed, and the reagents are passed through it from top to bottom, or in the form of a mobile bed in which the catalyst and reagents pass through the reactor in the same direction or counter-current.

EXAMPLE 1

Preparation of montmorillonite containing pillars of alumina (N-Al-PILC)

250 ml of a 1M solution of NaOH are added, at room temperature, to 500 ml of a 0.25M solution of $AlCl_3$. The resulting solution is maintained under stirring for 5 hours at 50° C.

A suspension of 10 g of montmorillonite in 1250 ml of water is prepared at room temperature. The temperature of the suspension is brought to 50° C. and, the solution prepared previously is added under stirring. After stirring for 3 hours the solid is separated by centrifugation and washed to eliminate the chloride ions. The montmorillonite containing polyoxoaluminium ions thus obtained, in humid form (water content 87% by weight), is then dried, first at room temperature and then at 100° C. for an hour, and then calcined at 400° C. in air for 5 hours. From 10 g of starting material 14.3 g of montmorillonite with pillars of alumina (N-Al-PILC) are obtained.

EXAMPLE 2

Preparation of mixtures of Y zeolite-montmorillonite with pillars of alumina (MZ-1 and MZ-2)

The catalyts MZ-1 and MZ-2 are prepared by the mechanical mixing in a damp atmosphere, in a ball-mill, of Y zeolite (Y HSZ 330HUA Tosoh Corporation, $SiO_2/Al_2O_3=6.18$, $Na_2O=0.28\%$) and the montmorillonite containing polyoxoaluminium ions, in humid form (water content 87% by weight), of example 1. In particular the catalyst MZ-1 is prepared by mixing 10 g of Y zeolite with 80 g of nontmorillonite containing polyoxoaluminium ions in humid form and the catalyst MZ-2 is prepared by mixing 4.3 g of Y zeolite with 80 g of montmorillonite containing polyoxoaluminium ions in humid form.

The mixtures thus prepared are dried in air at 100° C. and calcined at 400° C. in air for 5 hours. The composition of the catalysts MZ-1 and MZ-2 is shown in the following table:

| catalyst | % weight Y zeolite | % weight N-Al-PILC |
|---|---|---|
| MZ-1 | 50 | 50 |
| MZ-2 | 30 | 70 |

EXAMPLE 3

Preparation of a mixture of Y Zeo-lite/Filtrol 13 (FZ-1)

The catalyst FZ-1 is prepared by the mechanical mixing in a ball-mill of Y zeolite (Y HSZ 330 HUA Tosoh Corporation) and Filtrol Grade 13 clay (Engelhard), an acid clay obtained by treatment with mineral acid of calcium-montmorillonite, in equal weight quantities. The resulting mixture is dried at 100° C. and calcinated at 400° C. in air.

EXAMPLE 4

Alkylation test

For this test a plant is used with a stainless steel tubular reactor having an internal diameter of 1 cm, equipped with control mechanisms for the temperature and pressure. Inside the reactor, in fact, there is thermometric steel jacket of 0.3 cm in diameter inside of which is a thermocouple for reading the temperature of the catalytic bed at various degrees. The pressure control is carried out by means of a relief valve situated outside the reactor. The process is carried out at a pressure of 28 bar and a temperature of 154° C.

The catalyst MZ-1 of example 2, in the form of granules with dimensions of 20–40 mesh, in a quantity equal to 3 g, is charged into the reactor to form a bed of about 5 cm in height.

The alkylation reaction, is carried out in a liquid phase, by regulating the process conditions.

The feeding of the reagents is carried out from the upper part of the reactor and consists in a mixture of olefins-paraffins added to benzene, in a molar ratio benzene/olefins of 15:1. The feeding is effected from a tank in which it is kept under anhydrous conditions by the use of molecular sieves.

The composition of the olefin-paraffin mixture is shown in the following table:

| Components | weight % |
|---|---|
| n-$C_{10}$ paraffins | 8.49 |
| n-$C_{11}$ paraffins | 33.31 |
| n-$C_{12}$ paraffins | 24.34 |

| Components | weight % |
|---|---|
| n-$C_{13}$ paraffins | 16.44 |
| total paraffins | 82.58 |
| n-$C_{10}$ olefins | 0.89 |
| n-$C_{11}$ olefins | 3.68 |
| n-$C_{12}$ olefins | 3.48 |
| n-$C_{13}$ olefins | 3.18 |
| total olefins | 11.23 |
| aromatics | 4.19 |
| di-olefins | 0.10 |
| others | 1.90 |

The quantity of olefins at the inlet of the reactor is controlled by measuring the bromine number in the feeding; the conversion is determined by measuring the bromine number of the flow at the exit. The process is carried out at $WHSV_{zeolite}$(hours$^{-1}$) of 1.35 (which means that the whole flow rate refers only to the weight content of the Y zeolite in the catalyst) and at a $WHSV_{total}$(hours$^{-1}$) of 0.67. The catalyst is preactivated in a nitrogen flow at a temperature of 320–330° C. to eliminate residual traces of water. The heating of the reactor is carried out by a tubular electric oven and the temperature regulation by means of a thermocouple inside the oven.

The results obtained are summarized in the following table:

life time of catalyst MZ-1>200 hours, equivalent to 328 ml of processed feeding per gram of zeolite (ml feed./g zeolite)

| reaction time (hrs) | conversion (%) | LAB linearity (%) |
|---|---|---|
| 44.2 | 100 | 95 |
| 140 | 100 | 93 |
| 190 | 100 | 92 | wherein:

conversion (% mol)=(moles olefins consumed/moles initial olefins) 0.100

LAB linearity (%)=(moles linear monoalkylbenzenes produced/moles monoalkylbenzenes produced) 0.100 catalyst life (hrs)=period of time in which the catalyst maintains a conversion value>99%

In this example the catalyst life time is greater (>) than 200 hours: this means that for this period of time there was no deactiviation.

EXAMPLE 5

Alkylation test

The process described in example 4 above is repeated using the catalyst MZ-2 prepared in example 2, as catalyst.

The results obtained are summarized in the following table:

life time of catalyst MZ-2>250 hours, equivalent to 427 ml of processed feeding per gram of zeolite (ml feed./g zeolite)

| reaction time (hrs) | conversion (%) | LAB linearity (%) |
|---|---|---|
| 44.9 | 100 | 95 |
| 140 | 100 | 93.5 |
| 190 | 100 | 92 |

EXAMPLE 6

Comparative alkylation test

The process described in example 4 above is repeated using a Y zeolite (Y 330 HUA, Tosoh Corporation), as catalyst.

The results obtained are summarized in the following table:
life time of catalyst=140 hours, equivalent to 230 ml of processed feeding per gram of zeolite (ml feed./g zeolite)

| reaction time (hrs) | conversion (%) | LAB linearity (%) |
|---|---|---|
| 17 | 100 | 95.8 |
| 65 | 100 | 92.7 |
| 140 | 99 | 91.7 |

It is evident from a comparison of these results with those shown in examples 4 and 5 that the catalytic mixture used in the present invention produces higher linearity values than those obtained with the Y zeolite as such, even after processing a considerably higher quantity of reagents, with respect to the zeolite content (ex.4: 328 ml of feeding processed/g of zeolite; ex.5: 427 ml feed/g zeolite).

EXAMPLE 7

Comparative alkylation test

The process described in example 4 above is repeated using the catalyst prepared in example 1, at a WHSV=0.61 hours$^{-1}$.

The results obtained are summarized in the following table:
life time of catalyst=70 hours, equivalent to 50 ml of processed feeding per gram of zeolite (ml feed./g zeolite)

| reaction time (hrs) | conversion (%) | LAB linearity (%) |
|---|---|---|
| 23 | 100 | 96.8 |
| 87 | 96 | 98.8 |
| 113 | 63.3 | 99.8 |

Also in this case, on comparing these results with those shown in examples 4 and 5, it is clear that the life time of the catalytic mixture used in the present invention, or the period of time in which the catalytic mixture maintains a conversion value>99% (ex.4: life time>200 hours; ex.5: life time>250 hours) is decisively higher than that of montmorillonite with pillars of alumina used alone.

EXAMPLE 8

Comparative alkylation test

The process described in example 4 above is repeated using as catalyst the mixture of Y zeolite and clay prepared in example 3 (FZ-1), at a WHSV=0.69 hours$^{-1}$ and a WHSV$_{zeolite}$=1.35 hours$^{-1}$, and at a pressure of 30 bar.

The results obtained are summarized in the following table:
life time of catalyst>80 hours, equivalent to 132 ml of processed feeding per gram of zeolite (ml feed./g zeolite)

| reaction time (hrs) | conversion (%) | LAB linearity (%) |
|---|---|---|
| 18.8 | 100 | 93.3 |
| 42.8 | 100 | 91.5 |
| 73 | 100 | 89.7 |

On comparing these results with those shown in examples 4 and 5, it is clear that the catalytic mixture used in the present invention produces higher linearity and life time values than those obtained with a mixture of Y zeolite and clay such as montmorillonite as such, or not subjected to pillaring treatment.

EXAMPLE 9

Comparative alkylation test

The process described in example 4 above is repeated using as catalyst a Y zeolite (Y 330 HUA, Tosoh Corporation), at a temperature of 185° C., pressure of 30 bars and WHSV of 0.63 hours$^{-1}$.

The results obtained are summarized in the following table:
life time of catalyst>280 hours, equivalent to 230 ml of processed feeding per gram of zeolite (ml feed./g zeolite)

| reaction time (hrs) | conversion (%) | LAB linearity (%) |
|---|---|---|
| 46 | 100 | 88.8 |
| 118 | 100 | 86.6 |
| 214 | 100 | 84.7 |

It is evident from the comparison of these results with those shown in example 6, that an increase in temperature causes an increase in the life time of the catalyst but a considerable decrease in linearity.

EXAMPLE 10

Comparative alkylation test

The process described in example 4 above is repeated using as catalyst N-Al-Pilc prepared in example 1, at a temperature of 185° C., pressure of 25 bars and WHSV of 0.63 hours$^{-1}$.

The results obtained are summarized in the following table:
life time of catalyst>210 hours, equivalent to 200 ml of processed feeding per gram of zeolite (ml feed./g zeolite)

| reaction time (hrs) | conversion (%) | LAB linearity (%) |
|---|---|---|
| 46 | 100 | 91.3 |
| 118 | 100 | 90 |
| 210 | 99.2 | 89.5 |

Also for this catalyst an increase in temperature causes an increase in the life time but a considerable decrease in the linearity.

EXAMPLE 11

Comparative alkylation test

The process described in example 4 above is repeated using as catalyst MZ-2 prepared in example 2, at a temperature of 185° C.

The results obtained are summarized in the following table:

life time of catalyst MZ-2>360 hours, equivalent to 600 ml of processed feeding per gram of zeolite (ml feed./g zeolite)

| reaction time (hrs) | conversion (%) | LAB linearity (%) |
|---|---|---|
| 46.3 | 100 | 87.3 |
| 140 | 100 | 85.9 |
| 190 | 100 | 85.5 |

Also for this catalyst an increase in temperature is reflected in the life time of the catalyst but there is a considerable increase in linearity.

From the previous examples 9, 10 and 11 it can therefore be seen that the best results, above all with respect to the linearity, in the alkylation of aromatics with olefins are obtained when a mixture of Y zeolite and a smectite containing pillars of alumina is used as catalyst and the operating temperature is between 120 and 160° C., at which the catalytic mixture shows an unexpected synergetic effect.

We claim:

1. A process for the alkylation of aromatic hydrocarbons, comprising:

reacting an aromatic hydrocarbon with a linear olefin containing from 8 to 16 carbon atoms or mixtures thereof in a liquid phase under anhydrous conditions at a temperature of 120° C. to 160° C. in the presence of a catalyst comprising a mixture of a Y zeolite and a smectite containing pillars of aluminum oxide, wherein the weight ratio of Y zeolite to smetite with pillars of alumina ranges from 0.1 to 10.

2. The process of claim 1, wherein said weight ratio ranges from 0.3 to 1.5.

3. The process of claim 1, wherein said smectite is bentonite, montmorillonite or beidelite.

4. The process of claim 1, wherein said temperature of reaction ranges from 140° C. to 160° C.

5. The process of claim 1, wherein said aromatic hydrocarbon is a monocyclic or polycyclic aromatic hydrocarbon.

6. The process of claim 5, wherein said aromatic hydrocarbon is benzene, toluene, xylenes, ethylbenzene, naphthalene, methylnaphthalenes, ethylnaphthalenes or anthracene.

7. The process of claim 6, wherein said aromatic hydrocarbon is benzene.

8. The process of claim 1, wherein said olefin or mixtures thereof is selected from the group consisting of olefins having from 10 to 13 carbon atoms.

9. The process of claim 1, which further comprises conducting the reaction at a pressure of 10 to 50 bars.

10. The process of claim 9, wherein said pressure ranges from 20 to 35 bars.

11. The process of claim 1, which further comprises conducting the reaction at a WHSV ranging from 0.1 to 10 hours$^{-1}$.

12. The process of claim 11, wherein said WHSV ranges from 0.3 to 2 hours$^{-1}$.

13. The process of claim 1, wherein the amounts of the organic reactants are such that the molar ratio of aromatic hydrocarbon to olefin ranges from 30 to 1.

14. The process of claim 13, wherein the molar ratio of aromatic hydrocarbon to olefin ranges from 20 to 1.

15. The process of claim 1, wherein said olefin(s) reactant is diluted with an n-paraffin having from 8 to 16 carbon atoms and wherein the weight ratio of olefin to n-paraffin from 1:1 to 1:20.

* * * * *

UNITED STATES PATENT AND TRADEMARK OFFICE
CERTIFICATE OF CORRECTION

PATENT NO. : 6,204,423 B1
DATED : March 20, 2001
INVENTOR(S) : Amarilli et al.

Page 1 of 1

It is certified that error appears in the above-identified patent and that said Letters Patent is hereby corrected as shown below:

<u>Title page,</u>
The CPA should read as follows:

-- [45] **Date of Patent: \*Mar. 20, 2001** --

-- [\*] Notice: This patent issued on a continued prosecution application filed under 37 CFR 1.53(d), and is subjuct to the twenty year patent term provisions of 35 U.S.C. 154(a)(2). --

Signed and Sealed this

Twenty-second Day of January, 2002

Attest:

Attesting Officer

JAMES E. ROGAN
*Director of the United States Patent and Trademark Office*